US009035087B2

(12) United States Patent
Maeba et al.

(10) Patent No.: US 9,035,087 B2
(45) Date of Patent: May 19, 2015

(54) PROCESS FOR PRODUCING POLYISOCYANATE

(75) Inventors: Koji Maeba, Kamisu (JP); Haruhiko Noguchi, Kashima (JP); Tatsuki Kamatsuki, Kashima (JP); Masaaki Sasaki, Kashima (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 12/741,792

(22) PCT Filed: Nov. 10, 2008

(86) PCT No.: PCT/JP2008/070418
§ 371 (c)(1),
(2), (4) Date: May 6, 2010

(87) PCT Pub. No.: WO2009/063828
PCT Pub. Date: May 22, 2009

(65) Prior Publication Data
US 2010/0249450 A1    Sep. 30, 2010

(30) Foreign Application Priority Data
Nov. 14, 2007   (JP) ................. 2007-295868

(51) Int. Cl.
C07C 265/14    (2006.01)
C07C 263/20    (2006.01)
B01D 3/14      (2006.01)

(52) U.S. Cl.
CPC ............... *C07C 263/20* (2013.01); *B01D 3/14* (2013.01); *B01D 3/141* (2013.01)

(58) Field of Classification Search
CPC ........................ C07C 265/14; C07C 263/20
See application file for complete search history.

(56) References Cited

U.S. PATENT DOCUMENTS

| 4,118,286 | A  | * | 10/1978 | Burns et al. ................ 203/89 |
| 6,803,483 | B2 |   | 10/2004 | Lokum et al. |
| 7,108,770 | B2 |   | 9/2006  | Grun et al. |
| 7,118,653 | B2 |   | 10/2006 | Brady et al. |
| 7,358,388 | B2 |   | 4/2008  | Woelfert et al. |
| 2003/0230476 | A1 | * | 12/2003 | Brady et al. ................ 203/100 |
| 2004/0092701 | A1 |   | 5/2004  | Koch et al. |
| 2004/0118672 | A1 |   | 6/2004  | Grun et al. |

(Continued)

FOREIGN PATENT DOCUMENTS

| JP | 61-161250   | 7/1986 |
| JP | 2002-128850 A | 5/2002 |

(Continued)

OTHER PUBLICATIONS

International Search Report mailed Dec. 9, 2008 received in PCT/JP2008/070418.

(Continued)

*Primary Examiner* — Fereydoun G Sajjadi
*Assistant Examiner* — Jennifer C Sawyer
(74) *Attorney, Agent, or Firm* — Foley & Lardner LLP

(57) ABSTRACT

A method for producing a polyisocyanate includes a purification step of purifying an unpurified polyisocyanate, the purification step including a tar ingredient removal step of removing tar ingredients from an unpurified polyisocyanate, and a distillation step of distilling the unpurified polyisocyanate from which tar ingredients have been removed through a dividing wall distillation column.

2 Claims, 1 Drawing Sheet

(56) References Cited

U.S. PATENT DOCUMENTS

| | | | |
|---|---|---|---|
| 2006/0135810 A1 | 6/2006 | Wolfert et al. | |
| 2007/0015934 A1 | 1/2007 | Wolfert et al. | |

FOREIGN PATENT DOCUMENTS

| | | | |
|---|---|---|---|
| JP | 2004-143173 A | 5/2004 |
| JP | 2004-155760 A | 6/2004 |
| JP | 2004-155761 A | 6/2004 |
| JP | 2006-510696 A | 3/2006 |
| JP | 2006-281083 A | 10/2006 |

OTHER PUBLICATIONS

Notification of Reasons for Refusal Japanese Patent Application No. 2007-295868 dated Jul. 2, 2013.

* cited by examiner

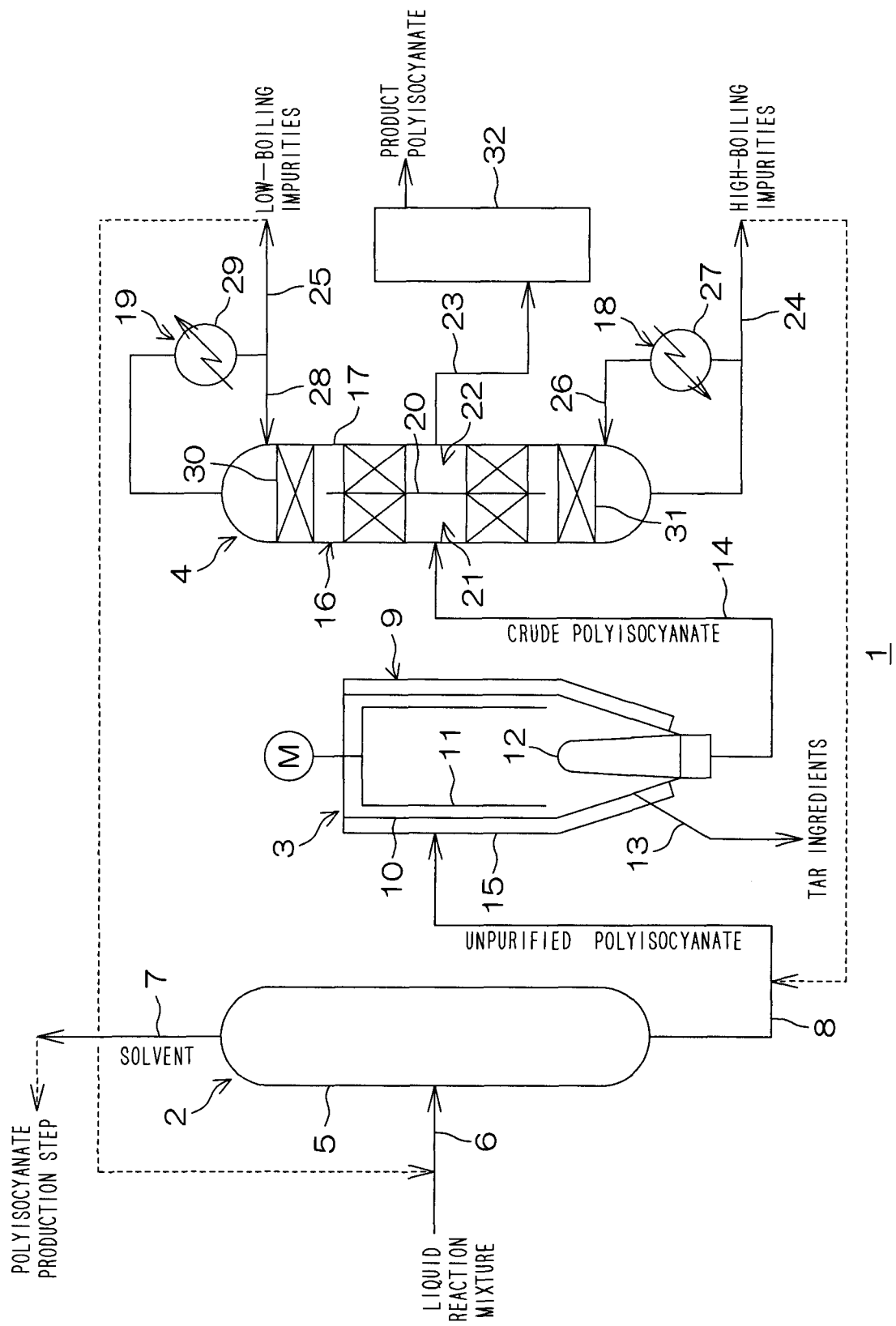

_US 9,035,087 B2_

PROCESS FOR PRODUCING POLYISOCYANATE

TECHNICAL FIELD

The present invention relates to a method for producing a polyisocyanate, and more specifically to a method for producing a polyisocyanate including a purification step of purifying an unpurified polyisocyanate.

BACKGROUND ART

Polyisocyanate, which is used as a raw material of polyurethane, is industrially produced, for example, by allowing polyamine and carbonyl chloride to react under a solvent.

In a polyisocyanate production plant, first, in a solvent recovery chamber, the solvent is removed from a reaction solution obtained by the above-mentioned reaction to obtain an unpurified polyisocyanate, and subsequently, in a distillation column, the unpurified polyisocyanate is purified by removing tar ingredients from the unpurified polyisocyanate (see, for example, the following Patent Document 1).

Further, in the distillation column, low boiling impurities and high boiling impurities are removed from the unpurified polyisocyanate from which tar ingredients have been removed (hereinafter referred to as crude polyisocyanate) to obtain a product polyisocyanate.

Patent Document 1: Japanese Unexamined Patent Publication No. 2006-281083

DISCLOSURE OF THE INVENTION

Problems to be Solved

However, the product polyisocyanate requires quality such as hue (coloring) and acidity. On the other hand, when the crude polyisocyanate is distilled, the distillation system is selected from a double-column system or a single-column system (side cut system).

With the double-column system, first, in a first distillation column, low boiling impurities are distilled off from the top of the column while the crude polyisocyanate containing high boiling impurities is discharged from the bottom thereof, and subsequently, in a second distillation column, the high boiling impurities are removed off from the bottom of the column while a product polyisocyanate is discharged from the top thereof.

Since the double-column system includes two distillation columns, energy consumption becomes significant. Besides, regarding the quality, the product polyisocyanate has disadvantageously high acidity although less colored.

On the other hand, with the single-column system, low boiling impurities are distilled off from the top of the distillation column, high boiling impurities are removed off from the bottom thereof, and a product polyisocyanate is discharged from the middle thereof.

Since the single-column system includes one distillation column, energy consumption can be reduced as compared with the double-column system. However, regarding the quality, the product polyisocyanate is disadvantageously colored and has high acidity.

It is an object of the present invention to provide a method for producing a polyisocyanate, the method capable of producing a product polyisocyanate with little coloring and low acidity while achieving reduction in energy consumption and purification of an unpurified polyisocyanate.

Means for Solving the Problem

To achieve the above object, the method for producing a polyisocyanate according to the present invention includes a purification step of purifying an unpurified polyisocyanate, the purification step including a tar ingredient removal step of removing tar ingredients from an unpurified polyisocyanate, and a distillation step of distilling the unpurified polyisocyanate from which tar ingredients have been removed through a dividing wall distillation column.

In the method for producing a polyisocyanate according to the present invention, it is preferable that the purification step includes a solvent removal step of removing a solvent from a reaction solution containing a solvent and an unpurified polyisocyanate as a preceding step of the tar ingredient removal step.

In the method for producing a polyisocyanate according to the present invention, it is preferable that a product polyisocyanate obtained after the distillation step has an acidity of 50 ppm or less.

In the method for producing a polyisocyanate according to the present invention, it is preferable that a polyisocyanate discharge temperature is from 100 to 200° C. in the distillation step.

In the method for producing a polyisocyanate according to the present invention, it is preferable that the purification step includes a cooling step of cooling a polyisocyanate discharged by distillation as a post step of the distillation step, and a residence time from the distillation step to the cooling step is 30 minutes or less.

Effect of the Invention

According to the method for producing a polyisocyanate of the present invention, in the tar ingredient removal step, tar ingredients are removed from an unpurified polyisocyanate, and subsequently, in the distillation step, the unpurified polyisocyanate from which tar ingredients have been removed is distilled through a dividing wall distillation column.

In the distillation step, since the dividing wall distillation column is used for distillation, energy consumption can be reduced as compared with a double-column system.

Further, when the unpurified polyisocyanate from which tar ingredients have already been removed is distilled through the dividing wall distillation column, a product polyisocyanate with less coloring and low acidity can be discharged.

BRIEF DESCRIPTION OF THE DRAWINGS

FIG. 1 is a schematic configurational diagram illustrating an embodiment of a purification system used in the method for producing a polyisocyanate according to the present invention.

EMBODIMENT OF THE INVENTION

FIG. 1 is a schematic configurational diagram illustrating an embodiment of a purification system used in the method for producing a polyisocyanate according to the present invention. An embodiment of the method for producing a polyisocyanate according to the present invention will be described below with reference to this purification system 1.

In FIG. 1, the purification system 1 is provided for a purification step of purifying an unpurified polyisocyanate, which is subsequent to the step of producing a polyisocyanate in a polyisocyanate production plant.

The purification system 1 includes a desolvating apparatus 2, a tar cutting apparatus 3, and a purifying apparatus 4.

The desolvating apparatus 2 is not particularly limited as long as a reaction solution can be separated into a solvent and an unpurified polyisocyanate, and for example, it is composed of a distillation column 5. The distillation column 5 may be a simple distillation column, or may be a tray or a packed distillation column designed with the required number of theoretical plates. Further, the distillation column 5 usually includes a reboiler and a condenser on its bottom and top, respectively, though not shown.

The middle tray (middle portion), top, and bottom of the distillation column 5 are connected to a feed pipe 6, an upstream end portion of a distillate discharge pipe 7, and an upstream end portion of a bottoms discharge pipe 8, respectively. A downstream end portion of the distillate discharge pipe 7 is used for drainage or returned to the polyisocyanate production step as shown by dotted lines.

A reaction solution is fed from the feed pipe 6 to the distillation column 5. In the polyisocyanate production step, the reaction solution contains, for example, a polyisocyanate produced by a reaction between carbonyl chloride and polyamine, and a solvent used for the reaction. The reaction solution, from which preferably, excessive carbonyl chloride and a by-product, hydrogen chloride gas have been removed as off gas after the reaction, specifically contains 5 to 40% by weight of a polyisocyanate and 60 to 95% by weight of a solvent, and further contains carbonyl chloride, hydrogen chloride, tar ingredients, and impurities each in a small amount.

Polyisocyanate varies depending on the production plant, and examples thereof include aromatic diisocyanates such as tolylene diisocyanate (TDI) and polymethylene polyphenylene polyisocyanate (MDI); aralkyl diisocyanates such as xylylene diisocyanate (XDI) and tetramethylxylylene diisocyanate (TMXDI); alicyclic diisocyanates such as bis(isocyanatomethyl)norbornane (NBDI), 3-isocyanatomethyl-3,5,5-trimethyl cyclohexylisocyanate (IPDI), 4,4'-methylene-bis (cyclohexyl isocyanate) ($H_{12}MDI$) and bis(isocyanatomethyl)cyclohexane ($H_6XDI$); aliphatic diisocyanates such as hexamethylene diisocyanate (HDI), and polymethylene polyphenyl polyisocyanates (crude MDI, polymeric MDI).

The solvent is an organic solvent inert to carbonyl chloride, polyamine, and polyisocyanate, and examples thereof include aromatic hydrocarbons such as toluene and xylene; halogenated aromatic hydrocarbons such as chlorotoluene, chlorobenzene, and dichlorobenzene; esters such as butyl acetate and amyl acetate; and ketones such as methyl isobutyl ketone and methyl ethyl ketone. Among them, chlorobenzene or dichlorobenzene is preferable.

The tar ingredients, which are polyisocyanate residues primarily containing a high molecular weight polyisocyanate, contain a dimer, trimer or higher multimer of polyisocyanate, or carbodiimide, urethodione, and uretonimine.

Then, the reaction solution is continuously fed from the feed pipe 6 into the distillation column 5. In the distillation column 5, the bottom thereof is heated (e.g., at 150 to 200° C.) with a reboiler (not shown) and decompressed (e.g., at 5 to 20 kPa) so that the reaction solution is boiled. As factors such as type and concentration of the polyisocyanate or solvent contained in the reaction solution, desired concentration of the polyisocyanate in the bottoms, and form and capacity of the distillation column 5 are judged in a comprehensive manner, the bottom temperature and the pressure reduction degree in the distillation column 5 is appropriately selected from the above range.

At the bottom of the distillation column 5, unpurified polyisocyanate which is rich in polyisocyanate or tar ingredients is discharged as bottoms and continuously flown out to the bottoms discharge pipe 8.

At the top of the distillation column 5, the solvent or chlorine-containing gas such as hydrogen chloride and carbonyl chloride is discharged as a distillate and continuously flown out from the distillate discharge pipe 7.

Thus, in the desolvating apparatus 2, the solvent is removed from the reaction solution and the unpurified polyisocyanate is discharged as bottoms (solvent removal step).

In the unpurified polyisocyanate thus discharged as bottoms, for example, the content ratio of the polyisocyanate ranges from 90 to 99% by weight and the content ratio of the tar ingredients ranges from 1 to 10% by weight. The unpurified polyisocyanate also contains the solvent in a proportion of 9% by weight or less and has an acidity of 0.05 to 0.2%.

The tar cutting apparatus 3 is not particularly limited as long as the unpurified polyisocyanate can be separated into a crude polyisocyanate and tar ingredients, and is composed of, for example, an evaporator 9. The evaporator 9 is, for example, a thin-film evaporator, though not limited thereto and includes a wiper 11 and an internal condenser 12 in a casing 10.

The casing 10 is formed in a sealed cylindrical shape having a lower portion formed in a funnel shape. The peripheral side wall of the casing 10 is connected to a downstream end portion of the bottoms discharge pipe 8. The lower side wall of the casing 10 is connected to an upstream end portion of a high boiling fraction discharge pipe 13. In this connection, a downstream end portion of the high boiling fraction discharge pipe 13 is used for drainage. Further, the bottom wall of the casing 10 is connected to an upstream end portion of a low boiling fraction discharge pipe 14. The casing 10 is connected to a vacuum suction pipe (not shown) for reducing pressure in the casing 10.

The wiper 11 is arranged in opposed relation to the inner peripheral surface of the peripheral side wall of the casing 10 at a slight gap and is provided so as to circumferentially rotate by drive of a motor M.

The internal condenser 12 is composed of a heat exchanger through which a refrigerant circulates, arranged on the bottom wall along the axial direction of the casing 10, and is connected to the low boiling fraction discharge pipe 14.

A jacket 15 for heating the inside of the casing 10 is provided on the outer peripheral surface of the peripheral side wall of the casing 10.

The unpurified polyisocyanate that continuously flows out from the distillation column 5 to the bottoms discharge pipe 8 is then flown into the casing 10.

In the casing 10, the drive of the motor M circumferentially moves the wiper 11 at a slight gap from the inner peripheral surface of the peripheral side wall of the casing 10. In addition, the inside of the casing 10 is reduced in pressure to 0.01 to 20 kPa by the vacuum suction pipe (not shown) and is heated to 80 to 230° C. by the jacket 15.

When the unpurified polyisocyanate flows into the casing 10, a centrifugal force of the wiper 11 that is circumferentially moving causes the unpurified polyisocyanate to be formed in a film of liquid in the gap between the wiper 11 and the inner peripheral surface of the peripheral side wall of the casing 10. Then, a crude polyisocyanate contained in the film of liquid evaporates by heating with the jacket 15, condensed by the internal condenser 12, discharged as a low boiling fraction, and flown out from the low boiling fraction discharge pipe 14.

On the other hand, tar ingredients contained in the film of liquid are condensed as are without evaporating from the film of liquid, discharged as a high boiling fraction, and then flown out of the high boiling fraction discharge pipe 13.

Thus, in the tar cutting apparatus 3, the tar ingredients are removed from the unpurified polyisocyanate and the crude polyisocyanate (i.e., the unpurified polyisocyanate from which tar ingredients have been removed) is discharged as a low boiling fraction (tar ingredient removal step).

The crude polyisocyanate thus discharged as a low boiling fraction contains a polyisocyanate in a proportion of 90 to 99.5% by weight, low boiling impurities other than the polyisocyanate (including a solvent or, when the polyisocyanate is, for example, TDI, chlorotoluene isocyanate) in a proportion of 10% by weight or less, and high boiling impurities (including ethylbenzene diisocyanate when the polyisocyanate is, for example, TDI) in a proportion of 0.01 to 1% by weight, and has an acidity of 100 to 500 ppm.

The tar cutting apparatus 3 is not limited to the thin-film evaporator equipped with the internal condenser as described above, and can also be composed of a thin-film evaporator equipped with an external condenser, a multipipe falling film evaporator, or the like.

The purifying apparatus 4 includes a dividing wall distillation column 16 and a cooling device 32.

The dividing wall distillation column 16 includes a distillation column 17, a heating unit 18, and a cooling unit 19.

The distillation column 17 is composed of a tray or a packed distillation column which is designed with the required number of theoretical plates. For example, the upper portion in the distillation column 17 is provided with an upper packed bed 30 at a position downward from the top of the column, and the lower portion in the distillation column 17 is provided with a lower packed bed 31 at a position upward from the bottom of the column. The upper packed bed 30 and the lower packed bed 31 are filled with regular packing or irregular packing. The number and arrangement of the packed beds are appropriately selected, and two packed beds are arranged at a spaced interval to each other in the vertical direction in each of a feed-side space 21 and a discharge-side space 22 to be described later.

In the distillation column 17, the middle portion between the upper packed bed 30 and the lower packed bed 31 is provided with a dividing wall 20. In the middle portion, the dividing wall 20 is positioned along the diametrical direction in the distillation column 17 so as to partition the inside of the distillation column 17. This divides the middle portion of the distillation column 17 into two, i.e., the feed-side space 21 and the discharge-side space 22, in the vertical direction.

In the middle portion of the distillation column 17, a downstream end portion of the low boiling fraction discharge pipe 14 is connected to the feed-side space 21, and an upstream end portion of a product discharge pipe 23 is connected to the discharge-side space 22.

The upstream end portion of the product discharge pipe 23 is provided in a position where the product polyisocyanate can be discharged at a temperature of 100 to 200° C., or preferably 160 to 190° C. in the vertical direction of the distillation column 17. The downstream end portion of the product discharge pipe 23 is connected to the cooling device 32. The inner diameter and the full length of the product discharge pipe 23 are set such that the product polyisocyanate can be left undischarged between the distillation column 17 and the cooling device 32 for a residence time of 30 minutes or less, preferably 15 minutes or less, or more preferably 10 minutes or less.

The bottom of the distillation column 17 is connected to an upstream end portion of the bottoms discharge pipe 24. In this connection, a downstream end portion of the bottoms discharge pipe 24 is used for drainage or connected on the way of the bottoms discharge pipe 8 in order to redistill the bottoms, as shown by dotted lines.

The top of the distillation column 17 is connected to an upstream end portion of a distillate discharge pipe 25. In this connection, a downstream end portion of the distillate discharge pipe 25 is used for drainage or connected on the way of the feed pipe 6 in order to redistill the distillate, as shown by dotted lines.

The heating unit 18 includes a heating circulating line 26 and a heater 27. An upstream end portion of the heating circulating line 26 is connected on the way of the bottoms discharge pipe 24. A downstream end portion of the heating circulating line 26 is connected to the bottom of the distillation column 17. The heater 27 is composed of a reboiler (a heat exchanger) to which a heating medium is fed, and is interposed on the way of the heating circulating line 26. In the heating unit 18, the temperature of the heating medium at the heater 27 is set in the range of, for example, 200 to 260° C. and the bottoms that circulates through the heating circulating line 26 is heated.

The heating unit 18 can also be composed of a heating pot equipped with a jacket or a coil to which a heat medium is fed.

The cooling unit 19 includes a cooling circulating line 28 and a cooler 29. An upstream end portion of the cooling circulating line 28 is connected on the way of the distillate discharge pipe 25. A downstream end portion of the cooling circulating line 28 is connected to the top of the distillation column 17. The cooler 29 is composed of a condenser (a heat exchanger used as a condenser) from which a refrigerant is fed, and is interposed on the way of the distillate discharge pipe 25 on the upstream side from the connection portion of the cooling circulating line 28. In the cooling unit 19, the cooling temperature of the cooler 29 is set in the range of, for example, 50 to 150° C., and a distillate which flows out into the distillate discharge pipe 25 is cooled.

The cooling unit 19 can also be composed without providing the cooling circulating line 28.

Then, in the distillation column 17, the bottom of the column is heated by the heating unit 18 (e.g., 160 to 200° C.) and is subjected to pressure reduction (e.g., at 5 to 20 kPa) so that a crude polyisocyanate is boiled. As factors such as type and concentration of the polyisocyanate contained in the crude polyisocyanate, desired purity of the product polyisocyanate to be discharged, and form and capacity of the distillation column 17 are judged in a comprehensive manner, the bottom temperature and the pressure reduction degree in the distillation column 17 are appropriately selected from the above range.

The crude polyisocyanate that is continuously flown out from the evaporator 9 into the low boiling fraction discharge pipe 14 is flown into the feed-side space 21 of the distillation column 17. In the feed-side space 21, high boiling impurities and a component rich in polyisocyanate in the crude polyisocyanate descends toward the bottom of the column, while low boiling impurities and a component rich in polyisocyanate in the crude polyisocyanate ascends toward the top of the column.

At the bottom of the distillation column 17, the high boiling impurities are discharged as bottoms and continuously flown out from the bottoms discharge pipe 24. A part of the bottoms is heated by the heater 27 and refluxed from the heating circulating line 26 to the bottom of the column. Thus, the bottom of the column is heated by the heating unit 18. Moreover, at the bottom of the distillation column 17, heating of the above-mentioned heating unit 18 causes the component rich in polyisocyanate to ascend into the feed-side space 21 and the discharge-side space 22.

At the top of the distillation column 17, the low boiling impurities are discharged as a distillate, which is continuously flown out from the distillate discharge pipe 25. A part of the distillate cooled by the cooler 29 is refluxed from the cooling circulating line 28 to the top of the column. Thus, the top of the column is cooled by the cooling unit 19. Moreover, at the top of the distillation column 17, the cooling of the above-mentioned cooling unit 19 causes the component rich in polyisocyanate to descend into the feed-side space 21 and the discharge-side space 22.

Therefore, the component rich in polyisocyanate flows into the discharge-side space 22 of the distillation column 17. The component rich in polyisocyanate in the discharge-side space 22 is continuously discharged as a product polyisocyanate from the product discharge pipe 23. The product polyisocyanate contains a polyisocyanate at high purity level (e.g., a purity of 99 to 100% by weight, or preferably 99.5 to 100% by weight).

Thus, in the purifying apparatus 4, the product polyisocyanate is discharged by distilling the crude polyisocyanate through the dividing wall distillation column 16 (distillation step).

The cooling device 32 is not particularly limited as long as the product polyisocyanate can be cooled, and is composed of, for example, a cooler from which a refrigerant is fed. The cooling device 32 is connected to a downstream end portion of the product discharge pipe 23.

The product polyisocyanate discharged from the distillation column 17 is left undischarged for a residence time of 30 minutes or less in the product discharge pipe 23 and is then flown into the cooling device 32.

The product polyisocyanate discharged from the distillation column 17 has a relatively high temperature (at 100 to 200° C.). Therefore, the product polyisocyanate is discharged through the product discharge pipe 23 and is then immediately cooled, thereby suppressing a side reaction to prevent degradation of the product polyisocyanate.

Thereafter, the product polyisocyanate is cooled to 100° C. or lower, or preferably 60° C. or lower in the cooling device 32 and is thereafter provided as a product polyisocyanate.

Thus, the product polyisocyanate is cooled in the cooling device 32 (cooling step).

According to the above-mentioned method for producing a polyisocyanate, in the tar ingredient removal step, tar ingredients are removed from an unpurified polyisocyanate to discharge a crude polyisocyanate, and subsequently, in the distillation step, the crude polyisocyanate is distilled through the dividing wall distillation column 16 to discharge a product polyisocyanate.

In the distillation step, since the dividing wall distillation column 16 is used for distillation, energy consumption can be reduced as compared with a double-column system. Further, in the distillation step, since the crude polyisocyanate from which tar ingredients have already been removed is distilled through the dividing wall distillation column 16, a product polyisocyanate with less coloring and low acidity can be discharged.

In short, as for coloring, with a usual single-column system (side cut system), in the crude polyisocyanate that flows into the distillation column, the high boiling impurities are distributed to the bottom of the column, the low boiling impurities are distributed to the top of the column, and the product polyisocyanate is discharged from the middle portion without being processed. In this case, the product polyisocyanate contains many impurities (particularly, high boiling impurities), resulting in an increase in coloring.

On the other hand, in the above-mentioned method, the crude polyisocyanate flows into the feed-side space 21 of the dividing wall distillation column 16 and is distributed once to the bottom or the top of the column. Subsequently, the components rich in polyisocyanate therein flow into the discharge-side space 22. Therefore, the product polyisocyanate discharged from the product discharge pipe 23 contains few impurities (particularly, high boiling impurities), and as a result, a product polyisocyanate with little coloring can be discharged.

According to the above-mentioned method, the hue (Hazen unit) of the product polyisocyanate can be specifically set to 20 or less, or further 10 or less. The hue (Hazen unit) can be determined according to JIS K0071-1 (1998) Testing methods for colour of chemical products—Part 1: Estimation of colour in Hazen units.

As for acidity, with a double-column system, in a second distillation column, high boiling impurities are distilled off from the bottom of the column and a product polyisocyanate is discharged from the top of the column. In other words, since the product polyisocyanate is discharged at relatively low temperature, a by-product, carbamoyl chloride produced by a reaction between the product polyisocyanate and hydrogen chloride, which is a low boiling impurity, increases, resulting in an increase in acidity.

With the usual single-column system (side cut system), the product polyisocyanate is also discharged from the middle portion of the distillation column without being processed as described above. In other words, the product polyisocyanate is discharged while still containing a by-product, carbamoyl chloride. As a result, the acidity of the product polyisocyanate increases.

On the other hand, in the above-mentioned method, at the top of the column, the low boiling impurities continuously flow out from the distillate discharge pipe 25 while cooling of the cooling unit 19 causes the component rich in polyisocyanate to flow into the discharge-side space 22. Then, the component rich in polyisocyanate is continuously discharged as a product polyisocyanate from the product discharge pipe 23 arranged in the middle portion of the distillation column 17.

Thus, in the above-mentioned method, since the hydrogen chloride that produces carbamoyl chloride as a by-product is discharged from the top of the column, the hydrogen chloride contained in the component rich in polyisocyanate can be reduced. In addition, since the product discharge pipe 23 is arranged in the middle portion of the distillation column 17, it can discharge the product polyisocyanate at relatively high temperature as compared with the case where the product discharge pipe 23 is arranged at the top of the column. This can suppress the reaction between the product polyisocyanate and hydrogen chloride, which can reduce production of carbamoyl chloride.

In particular, since the product discharge pipe 23 is provided at a position where the product polyisocyanate can be discharged at 100 to 200° C., or preferably 160 to 190° C. in the vertical direction of the distillation column 17, the product polyisocyanate is discharged at the above-mentioned temperature. This can more suppress the reaction between the product polyisocyanate and hydrogen chloride, which can still further reduce the production of carbamoyl chloride. As a result, in the above-mentioned method, a product polyisocyanate with low acidity can be discharged.

According to the above-mentioned method, the acidity of the product polyisocyanate can be made specifically, to 50 ppm or less, further 20 ppm or less, or particularly 10 ppm or less. The acidity can be determined according to the acidity test for aromatic isocyanates described in Appendix 2 of JIS K 1556 (2006), Polyurethane raw materials—Testing methods for toluene diisocyanate.

EXAMPLES

The present invention will now be described in more detail by way of Example and Comparative Example.

Example 1

A product tolylene diisocyanate (TDI) was purified from a reaction solution using a purification system shown in FIG. 1.
1. Solvent Removal Step
First, in the distillation column 5 of the desolvating apparatus 2, a reaction solution (19% by weight of tolylene diisocyanate, 80% by weight of dichlorobenzene (DCB), 0.01% by weight of carbonyl chloride, and 1% by weight of tar ingredients) obtained in the production step was separated into an unpurified TDI and DCB under the following operating conditions.
(Operating Conditions of Distillation Column 5)
  Temperature on the bottom of column: 180° C.
  Pressure reduction degree in the column: 10 kPa
  Amount of reaction solution fed: 200 kg/h
  Amount of bottoms (unpurified TDI) discharged: 50 kg/h
  Amount of distillate (DCB) discharged: 150 kg/h
The discharged unpurified TDI contained 96.3% by weight of TDI, 2.6% by weight of tar ingredients, and 0.5% by weight of DCB, and had an acidity of 0.1%.
2. Tar Ingredient Removal Step
Next, in the evaporator 9 (thin-film evaporator equipped with an internal condenser) of the tar cutting apparatus 3, the unpurified TDI thus discharged was separated into a crude TDI and tar ingredients under the following operating conditions.
(Operating Conditions of Evaporator 9)
  Jacket-heating temperature: 200° C.
  Pressure reduction degree in the casing: 1 kPa
  Amount of unpurified TDI fed: 50 kg/h
  Amount of high boiling fraction (tar ingredients) discharged: 1 kg/h
  Amount of low boiling fraction (crude TDI) discharged: 49 kg/h
The crude TDI thus discharged contained 98.7% by weight of TDI, 0.1% by weight of high boiling impurities, and 1.2% by weight of low boiling impurities (including a solvent), and had an acidity of 150 ppm.
3. Distillation Step and Cooling Step
Next, the crude TDI thus discharged was separated into a product TDI, and high boiling impurities and low boiling impurities in the dividing wall distillation column 16 (packing material: 7 theoretical plates×3 beds, product discharge pipe: 187° C. position (lower portion of the second bed)) of the purifying apparatus 4 under the following operating conditions (distillation step).
(Operating Conditions of Dividing Wall Distillation Column 16)
  Heat-medium temperature: 220° C.
  Cooler cooling temperature: 55° C.
  Temperature at the bottom of the column: 190° C.
  Pressure reduction degree in the column: 17 kPa
  Amount of crude TDI fed: 50.6 kg/h
  Amount of product TDI discharged: 46.7 kg/h
  Amount of bottoms (high boiling impurities) discharged: 2.2 kg/h
  Amount of distillate (low boiling impurities) discharged: 1.7 kg/h
The discharged product TDI was cooled to 60° C. or lower with the condenser 32 for a residence time of 7 minutes (cooling step).
The product TDI thus obtained had a purity of 99.5% by weight or more, a hue (Hazen unit) of 5 or less, and an acidity of 6 ppm.

Comparative Example 1

The product TDI was obtained in the same manner as in Example 1, except that in the distillation step, the crude TDI was separated into the product TDI, and high boiling impurities and low boiling impurities under the following operating conditions using a distillation column where the dividing wall 20 was removed from the dividing wall distillation column 16.
(Operating Conditions of Distillation Column (Without Partition Wall))
  Heat-medium temperature: 220° C.
  Cooler cooling temperature: 85° C.
  Temperature at the bottom of the column: 189° C.
  Pressure reduction degree in the column: 17 kPa
  Amount of crude TDI fed: 61.7 kg/h
  Amount of product TDI discharged: 56.9 kg/h
  Amount of bottoms (high boiling impurities) discharged: 2.7 kg/h
  Amount of distillate (low boiling impurities) discharged: 2.1 kg/h
The product TDI thus obtained had a purity of 99.5% by weight or more, a hue (Hazen unit) of 20 or more, and an acidity of 33 ppm.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The present invention is suitably used in order to industrially produce a polyisocyanate which is a raw material of polyurethane.

The invention claimed is:
1. A method for producing a toluene diisocyanate comprising a purification step of purifying an unpurified toluene diisocyanate, the purification step comprising:
  a solvent removal step of removing a solvent from a reaction solution containing the solvent and the unpurified toluene diisocyanate,
  a tar ingredient removal step of removing tar ingredients from an unpurified toluene diisocyanate as a post step of the solvent removal step,
  a distillation step of distilling, through a dividing wall distillation column, a crude toluene diisocyanate as the unpurified toluene diisocyanate from which tar ingredients have been removed as a post step of the tar ingredient removal step, and
  a cooling step of cooling the toluene diisocyanate discharged by distillation as a post step of the distillation step by a cooler, wherein the crude toluene diisocyanate to be fed to the dividing wall distillation column contains a toluene diisocyanate in a proportion of 90 to 99.5% by weight, the dividing wall distillation column is connected to the cooler though a product discharge pipe, a discharge temperature of the toluene diisocyanate from the dividing wall distillation column is from 160 to 190° C. in the distillation step, a residence time of the toluene diisocyanate in the product discharge pipe is 10 minutes or less, and the toluene diisocyanate is cooled to 100° C. or lower in the cooling step, wherein the toluene diisocyanate has a hue (Hazen unit) of 10 or less.

2. The method for producing the product toluene diisocyanate according to claim 1, wherein the product toluene diisocyanate obtained after the distillation step has an acidity of 50 ppm or less.

\* \* \* \* \*